(12) United States Patent
Wang et al.

(10) Patent No.: US 8,513,030 B2
(45) Date of Patent: Aug. 20, 2013

(54) CHIRALITY SENSOR AND METHOD FOR DETECTION OF AFLATOXIN BY USING THE SENSOR

(76) Inventors: Libing Wang, Wuxi (CN); Chuanlai Xu, Wuxi (CN); Zhou Xu, Wuxi (CN)

( * ) Notice: Subject to any disclaimer, the term of this patent is extended or adjusted under 35 U.S.C. 154(b) by 0 days.

(21) Appl. No.: 13/464,759

(22) Filed: May 4, 2012

(65) Prior Publication Data

US 2013/0071947 A1    Mar. 21, 2013

(51) Int. Cl.
*G01N 33/553* (2006.01)

(52) U.S. Cl.
USPC ........................................... 436/525

(58) Field of Classification Search
None
See application file for complete search history.

(56) References Cited

U.S. PATENT DOCUMENTS

| | | | |
|---|---|---|---|
| 4,818,687 A * | 4/1989 | Groopman et al. | 436/518 |
| 5,045,480 A * | 9/1991 | Johnson et al. | 436/532 |
| 6,485,703 B1 * | 11/2002 | Cote et al. | 424/9.1 |
| 6,855,551 B2 * | 2/2005 | Bawendi et al. | 436/6 |
| 2004/0091602 A1 * | 5/2004 | Hwang et al. | 427/2.11 |
| 2007/0105176 A1 * | 5/2007 | Ibey et al. | 435/14 |
| 2008/0050842 A1 * | 2/2008 | Golovlev et al. | 436/525 |
| 2009/0068637 A1 * | 3/2009 | Xia et al. | 435/5 |
| 2009/0196852 A1 * | 8/2009 | Watkinson | 424/85.4 |
| 2011/0097723 A1 * | 4/2011 | Liu et al. | 435/6 |
| 2012/0157328 A1 * | 6/2012 | Dudek et al. | 506/9 |

FOREIGN PATENT DOCUMENTS

CN    101315371 A  * 12/2008

OTHER PUBLICATIONS

Mastroianni, A.J. et al., "Pyramidal and chiral groupings of gold nanocrystals assembled using DNA scaffolds", J. American Chemical Society, (2009) 131:8455-8459.*
Anfossi, L. et al., "Homogeneous immunoassay based on gold nanoparticles and visible absorption detection", Anal. Bionanl. Chem., (2009), 394:507-512.*
Kaur, J. et al., "Immunochromatographic dipstick assay format using gold nanoparticles labeled protein-hapten conjugate for the detection of atrazine", Environ. Sci. Technol., (2007) 41:5028-5036.*
Claridge, S.A. et al., "Directed assembly of discrete gold nanoparticle groupings using branched DNA scaffolds", Chem. Mater. (2005) 17:1628-1635.*

* cited by examiner

*Primary Examiner* — Shafiqul Haq
*Assistant Examiner* — Gary E Hollinden
(74) *Attorney, Agent, or Firm* — Jacobson Holman PLLC; Jiwen Chen

(57) ABSTRACT

A universal chirality sensor based on immuno-recognition-driven nanoparticle assembly has been fabricated. The design of smart 10 nm AuNP-antigen and 20 nmAuNP-antibody described for the detection of aflatoxin B1. 10 nm AuNP-antigen and 20 nmAuNP-antibody assemble to symmetric plasmonic nanoparticle dimers, which induced CD signal. The addition of aflatoxin B1 to the chirality sensor resulted in transverse CD signal compared to a blank control as shown by CD measurements. This process also allowed the rapid and facile determination of concentrations of aflatoxin B1 in drinking water (tap water). Good linearity for all calibration curves was obtained, and the limit of detection (LOD) for aflatoxin B1 was 0.02 ng/mL in tap water.

7 Claims, 3 Drawing Sheets

US 8,513,030 B2

CHIRALITY SENSOR AND METHOD FOR DETECTION OF AFLATOXIN BY USING THE SENSOR

The present application claims the priority of Chinese Application No. 201110279477.4, filed Sep. 20, 2011 under 35 U.S.C. §119, which is hereby incorporated by reference.

TECHNICAL FIELD

The present invention relates to the construction of a chirality sensor for detection of aflatoxin B1. The chirality sensor according to the present invention is prepared based on the plasmonic asymmetric dimers assembled by the immunorecognition between gold nanoparticles coupled with antigen or antibody (one group of gold nanoparticles coupled with an antigen, the other group of gold nanoparticles coupled with an antibody to the antigen of the first group). It belongs to food safety detection field.

BACKGROUND OF THE INVENTION

Increasing attention is being paid to the chirality of nanomaterials, and focus is moving toward the application of nanostructural analyses, such as conformational studies of biomolecules upon interacting with nanoparticles, information about nanocarriers, analysis of DNA biofunction on nanoparticles, and nanomaterial assemblies. Among these areas, nanomaterial assemblies endowed with fascinating optical properties may be regarded as one of the most active fields of research. In optical spectroscopy, circular dichroism (CD) can be produced by molecular-recognition-driven assembly of plasmonic nanoparticles into chiral structures. Alivisatos and co-workers proposed the concept of chiral plasmonic nanostructures of Au NPs with tetrahedral symmetry, and more importantly, chiral enantiomers were successfully built by using four different sized Au NPs at the tips of a discrete pyramid. Tang's group has demonstrated that remarkable plasmonic CD signals could be produced in the visible light region based on the assembly of gold nanorods (Au NRs) and DNA hybrids. Govorov et al. proposed a theory to account for a plasmonic mechanism of optical activity in chiral complex assemblies composed of plasmonic nanoparticles. Their research demonstrated that the CD signal was very sensitive to the geometry. Our group has constructed multimeric assemblies of various geometries (ranging from dimers, trimers, and tetramers to very complex agglomerates) to achieve chiral assemblies with strong chiral optical activity by performing polymerase chain reaction (PCR) on the surfaces of Au NPs functionalized with primers. This unique optical property holds great promise for the fabrication of negative refractive index materials. Furthermore, the strong CD signal might also be exploited in the construction of smart sensors. Recently, research has been directed towards the detection of targets by utilizing the CD signal. For example, pairs of "right-handed" and "left-handed" molecules have been discriminated based on their interactions with chiral nanoparticles. Chiral Ag-1-cysteine complex nanoparticles have been prepared as a probe for $Hg^{2+}$; the displacement of $Ag^+$ from the chiral nanoparticles by $Hg^{2+}$ induced a conformational change of the ligands on the surface of the NPs. In order to achieve specific detection using this unique property, a universal model based on specific molecular recognition is needed. Seeking a suitable model of molecular recognition is of tremendous importance for devising a chirality detection platform.

Immuno-recognition has long been among the most popular affinity-based recognition targets. A wide variety of immunosensors based on antibodies has been reported, such as those for small organic molecules, proteins, viruses, bacteria, and metal ions. The main advantage of the use of antibodies as recognition targets is their sensitivity and selectivity. Moreover, many antibodies have become commercially available.

SUMMARY OF THE INVENTION

Accordingly, the invention is directed to a method of preparing the universal chirality detection sensor based on the fascinating CD properties arising from the immuno-recognition-driven nanoparticle assembly. Using aflatoxin B1 as a model target substrate, the invention establishes the method and technical parameters for the fast and sensitive aflatoxin B1 analysis by using this sensor.

The present invention provides the preparation method for aflatoxin B1 immunosensor, which involves electrostatic interactions between antibodies coupled with first gold nanoparticles and antigens coupled with second gold nanoparticles. After coupling, immuno-recognition driven to assemble plasmonic nanoparticles into chiral asymmetric dimers, thus we can obtain the specific biosensor for the determination of aflatoxin B1 by utilizing the CD signal. And the fabrication method comprises:

a) 10 nm gold nanoparticles are synthesized by reduction of $HAuCl_4$ using glycerite and trisodium citrate;

b) 20 nm gold nanoparticles are synthesized by reduction of $HAuCl_4$ using trisodium citrate;

c) The synthesized 10 nm gold nanoparticles based on step a), couple with coating-antigen (Ag) to form the complexes of Au NP-Ag through electrostatic interaction;

d) The synthesized 20 nm gold nanoparticles based on step a, couple with antibody (Ab) to form the complexes of Au NP-Ab through electrostatic interaction.

The application of the sensor for rapid detection of aflatoxin B1 is based on the CD intensity at 533 nm of the chiral asymmetric dimers.

The determination procedure is shown in FIG. 1. When the 10 nm Au NPs-Ag and 20 nm Au NPs-Ab were mixed in solution, dimers were assembled due to immuno-recognition between the antibody and antigen coating. The antibody is aflatoxin B1 antibody. The antigen is aflatoxin B1-ovalbumin (OVA). The CD signal was increased due to the formation of the asymmetric dimers. On the other hand, when the analyte aflatoxin B1 was added to this chirality sensor, the anti-aflatoxin B1 antibodies competitively recognized the aflatoxin B1 analyte and Au NP-Ag in solution, which maintained the dispersed state of the Au NPs and hence the CD signal was decreased. Thus, Au NPs-Ag and Au NPs-Ab can be used to detect the residues of aflatoxin B1 in tap water samples.

The quantification determination results show that the sensor is sensitive to aflatoxin B1 with a LOD of 0.02 ng/mL, which is comparable to those of the ELISA and chromatographic methods. The chirality detection platform based on immuno-recognition presented herein holds promise for superior universal application and better sensitivity. The aflatoxin B1 in a real sample showed no effect on the detection results of the chirality sensor, illustrating the excellent selectivity of the method. Application of the chirality sensor to real samples also showed good detection of the target aflatoxin B1. As these proof-of-concept experiments have shown, the chirality sensor could be used to detect various targets, provided that multiple antibodies could be generated and commercialized.

DETAILED DESCRIPTION OF THE INVENTION

Figure 1:
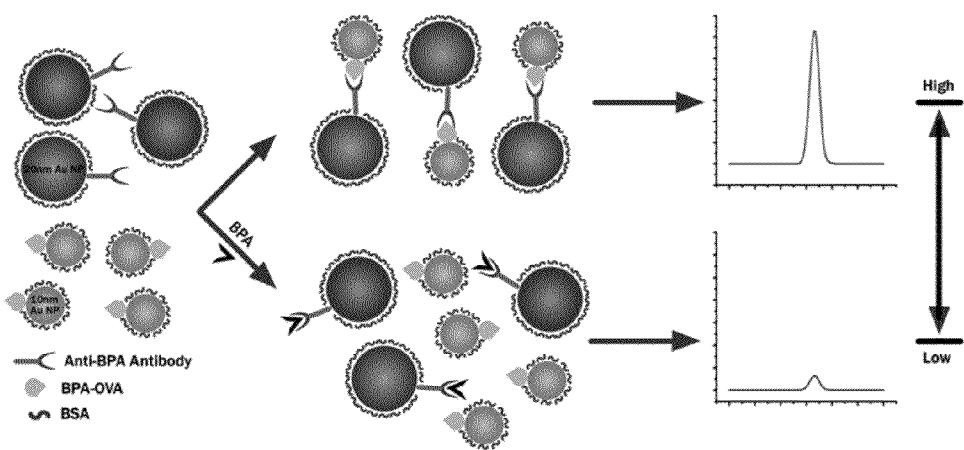
FIG. 1 show the scheme of the detection based on the formation of the magnetic aggregates. The dispersed Au NPs gradually assembled to be an asymmetric dimers state due to target (aflatoxin B1), which caused the changes in the CD signal of water.
Figure 2:
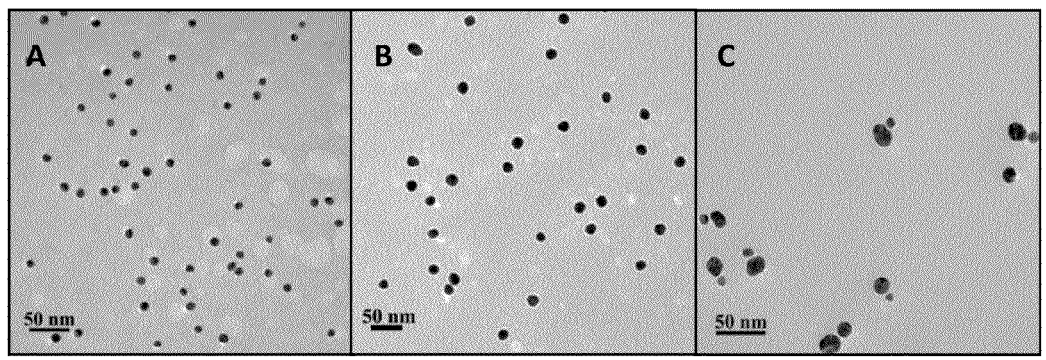
FIG. 2 shows the TEM images of the disperse 10 nm NP (A) and 20 nm NP (B) and the assembly of the asymmetric dimers (C).
Figure 3:
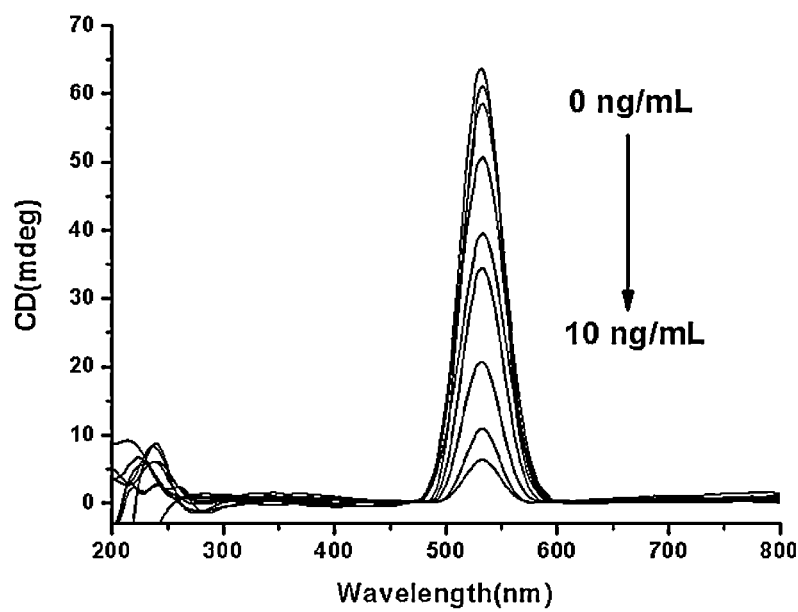
FIG. 3 shows CD spectral change with the concentration of aflatoxin B1.
Figure 4:
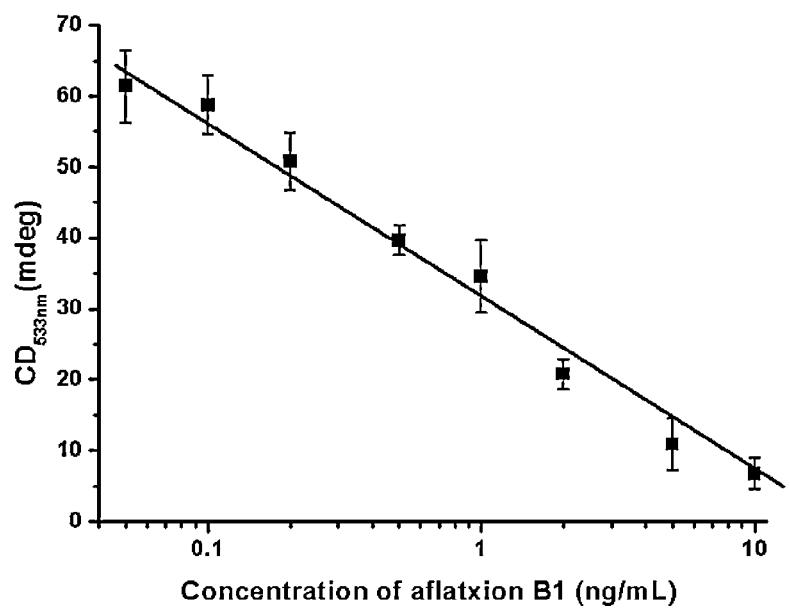
FIG. 4 shows the plot of decreased CD intensity (533 nm) as a function of logarithmic aflatoxin B1 concentration, showing good linearity up to 10 ng/mL.
Figure 5:
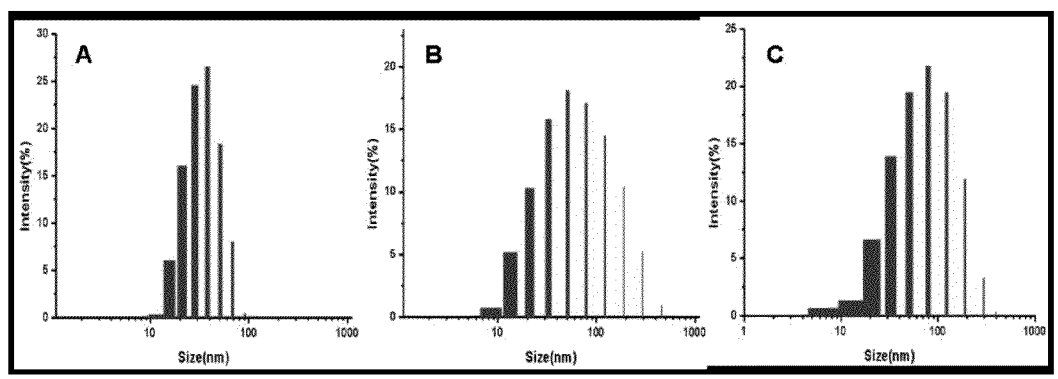
FIG. 5 shows hydrodynamic diameters of NPs at different states via dynamic light scattering (DLS). Mean average hydrodynamic diameters for (A) coating antigen modify 10 nm Au NP and (B) antibody modify 20 nm Au NP and (C) assemblies asymmetric dimer.

The detailed information of the invention is further described through the steps listed in the following text. All the reagents involved are analytical grade purify. Notably to mention that the following detailed steps are as exemplifications, while the present invention is not limited to the content as follows:

Step 1: Synthesis of 20 nm Gold Nanoparticles aqueous trisodium citrate solution (1.4 mL, 1% by weight, freshly prepared) is quickly added to a boiling aqueous solution of $HAuCl_4$ (87.5 mL, 0.01%) under vigorous stirring and reflux. After several minutes, the color of the solution changes from pale yellow to brilliant red. After boiling for 10 min, the heat source is removed to allow the reaction solution to cool to room temperature, diluting the solution to 100 mL, and it was subsequently stored at 4° C. The morphology of the dispersed 20 nm Au NPs was characterized by transmission electron microscopy (TEM).

Step 2: Synthesis of 10 nm Gold Nanoparticles 70 mL $HAuCl_4$ (0.01%) solution was prepared. A second solution containing 0.038 g trisodium citrate, 0.02 g tannic acid and 0.018 g potassium carbonate dissolved in 20 ml water was prepared. Both the solutions were heated to 60° C. with constant stirring. Then the second solution was added to $HAuCl_4$ solution. The solution was then boiled for 30 min to get the red colored colloid. And it was subsequently stored at 4° C. The morphology of the dispersed 10 nm Au NPs was characterized by transmission electron microscopy (TEM).

Step 3: preparation of Au NP-Ab

14 μL of 0.2 M $K_2CO_3$ solution was added to 200 μL of 20 nm Au NP solution. After allowing the mixture to react for about 5 min, 2.6 μL of a 10 μg/mL solution of anti-aflatoxin B1 antibodies was added and the resulting mixture was incubated for 1 h at room temperature with shaking The surfaces of the 20 nm Au NPs were then blocked with 10 μL of 100 μg/mL BSA solution, so as to prepare Au NP-Ab.

Step 4: Preparation of Au NP-Ag

18 μL of 0.2 M $K_2CO_3$ solution was added to 200 μL of 10 nm Au NP solution. After allowing the mixture to react for about 5 min, 2.6 μL of a 100 μg/mL solution of the coating antigen was added and the resulting mixture was incubated for 1 h at room temperature with shaking The surfaces of the 10 nm Au NPs were then blocked with 10 μL of 100 μg/mL BSA solution, so as to prepare Au NP-Ag.

Step 5: Detection Methods

The Au NP-Ab and Au NP-Ag solutions were centrifuged to remove the excess anti-aflatoxin B1 antibody, coating antigen, and BSA. After washing twice with pH 7.5 carbonate buffer, the Au NP-Ab and Au NP-Ag were combined in pH 7.5 carbonate buffer and made up to the appropriate volume for the next step. The antibodies and coating antigen adhered to the 10 nm Au NPs and 20 nm Au NPs, respectively, served to conjugate these particles in solution through electrostatic interaction.

Step 6: Structure Characterization Asymmetric Plasmonic Nanoparticle Dimer

The prepared asymmetric plasmonic nanoparticle dimer based on step 5 are charactering by transmission electron microscopy (TEM), light scattering instrument (DLS). Malvern Zetasizer nano instrument operating at a laser wavelength of 825-832 nm was used for particle size measurements in highly dilute aqueous gold dispersions. TEM analyses were also performed to determine the sizes of gold nanoparticles on a JEOL 2010 transmission electron microscope at an acceleration voltage of 200 kV. The samples for TEM were prepared by placing a drop of the nanoparticle solution on carbon coated copper grids.

While the foregoing embodiments of the invention have been illustrated and described, it will be appreciated that various changes can be made therein without departing from the spirit and scope of the invention.

The embodiments of the invention in which and exclusive properties or privilege is claimed are defined as follows.

The invention claimed is:

1. A method for making a chirality sensor kit for detection of aflatoxin B1 in tap water samples, comprising the steps of:
   (1) synthesizing 20 nm gold nanoparticles;
   (2) synthesizing 10 nm gold nanoparticles;
   (3) coupling the 20 nm gold nanoparticles with aflatoxin B1 antibodies to form complexes of Au NP-Ab through electrostatic interaction and
   (4) coupling the 10 nm gold nanoparticles with aflatoxin B1-ovalbumin to form the complexes of Au NP-Ag through electrostatic interaction.

2. The method of claim 1, wherein the synthesis of 20 nm gold nanoparticles comprises the following steps:
   adding an aqueous trisodium citrate solution (1.4 mL, 1% by weight, freshly prepared) to a boiling aqueous solution of $HAuCl_4$ (87.5 mL, 0.01%) under vigorous stirring and reflux;
   waiting for several minutes until the color of the solution changes from pale yellow to bright red;
   boiling the solution for 10 minutes;
   cooling the solution to room temperature;
   diluting the solution to 100 mL; and
   storing the solution at 4° C.

3. The method of claim 1, wherein the synthesis of 10 nm gold nanoparticles comprises the following steps:
   providing a first solution of 70 mL $HAuCl_4$ (0.01%);
   providing a second solution containing 0.038 g trisodium citrate, 0.02 g tannic acid and 0.018 g potassium carbonate dissolved in 20 ml water;
   heating both the first and second solutions to 60° C. with constant stirring;
   adding the second solution to the first solution to form a mixed solution;
   boiling the mixed solution for 30 min to obtain red colored colloid;
   storing the colloid at 4° C.

4. The method of claim 1, wherein the preparation of Au NP-Ab comprises the following steps:
adding 14 μL of 0.2 M $K_2CO_3$ solution to 200 μL of 20 nm Au NP solution to form a mixture;
after allowing the mixture to react for about 5 minutes, adding 2.6 μL of a 10 μg/mL solution of anti-aflatoxin B1 antibodies to the mixture;
incubating the mixture for 1 hour at room temperature with shaking;
blocking surfaces of the 20 nm Au NP-Ab with 10 μL of 100 μg/mL bovine serum albumin (BSA) solution.

5. The method of claim 1, wherein the preparation of Au NP-Ag comprises the following steps:
adding 18 μL of 0.2 M $K_2CO_3$ solution to 200 μL of 10 nm Au NP solution to form a mixture;
after allowing the mixture to react for about 5 minutes, adding 2.6 μL of a 100 μg/mL aflatoxin B1-ovalbumin solution and incubating the mixture for 1 hour at room temperature with shaking;
blocking the-surfaces of the 10 nm Au NP-Ag with 10 μL of 100 μg/mL BSA solution.

6. The method of claim 1, wherein the Au NP-Ab and Au NP-Ag solutions were centrifuged to remove the excess anti-aflatoxin B1 antibody, aflatoxin B1-ovalbumin, and BSA; after washing twice with pH 7.5 carbonate buffer, the Au NP-Ab and Au NP-Ag solutions were combined in pH 7.5 carbonate buffer.

7. The method of claim 1, wherein the synthesis of 20 nm gold nanoparticles comprises the following steps:
adding an aqueous trisodium citrate solution (1.4 mL, 1% by weight, freshly prepared) to a boiling aqueous solution of $HAuCl_4$ (87.5 mL, 0.01%) under vigorous stirring and reflux;
waiting for several minutes until the color of the solution changes from pale yellow to brilliant red;
boiling the solution for 10 minutes;
cooling the solution to room temperature;
diluting the solution to 100 mL;
and storing the solution at 4° C.;

wherein the synthesis of 10 nm gold nanoparticles comprises the following steps:
providing a first solution of 70 mL $HAuCl_4$ (0.01%);
providing a second solution containing 0.038 g trisodium citrate, 0.02 g tannic acid and 0.018 g potassium carbonate dissolved in 20 ml water;
heating both the first and second solutions to 60° C. with constant stirring;
adding the second solution to the first solution to form a mixed solution;
boiling the mixed solution for 30 min to obtain red colored colloid;
storing the colloid at 4° C.;
wherein the preparation of Au NP-Ab comprises the following steps:
adding 14 μL of 0.2 M $K_2CO_3$ solution to 200 μL of 20 nm Au NP solution to form a mixture;
after allowing the mixture to react for about 5 minutes, adding 2.6 μL of a 10 μg/mL solution of anti-aflatoxin B1 antibodies to the mixture;
incubating the mixture for 1 hour at room temperature with shaking;
blocking surfaces of the 20 nm Au NP-Ab with 10 μL of 100 μg/mL BSA solution;
wherein the preparation of Au NP-Ag comprises the following steps:
adding 18 μL of 0.2 M $K_2CO_3$ solution to 200 μL of 10 nm Au NP solution to form a mixture;
after allowing the mixture to react for about 5 minutes, adding 2.6 μL of a 100 μg/mL aflatoxin B1-ovalbumin solution and incubating the mixture for 1 hour at room temperature with shaking;
blocking surfaces of the 10 nm Au NP-Ag with 10 μL of 100 μg/mL BSA solution; and
wherein the Au NP-Ab and Au NP-Ag solutions were centrifuged to remove the excess anti-aflatoxin B1 antibody, aflatoxin B1-ovalbumin, and BSA; after washing twice with pH 7.5 carbonate buffer, the Au NP-Ab and Au NP-Ag solutions were combined in pH 7.5 carbonate buffer.

* * * * *